United States Patent [19]

Häfele et al.

[11] Patent Number: 5,546,787
[45] Date of Patent: Aug. 20, 1996

[54] HOUSING FOR GAS SENSORS

[75] Inventors: Edelbert Häfele, Karlsruhe; Walter Seeger, Gaggenau, both of Germany

[73] Assignee: Roth-Technik GmbH & Co., Gaggenau, Germany

[21] Appl. No.: 234,991

[22] PCT Filed: Feb. 16, 1993

[86] PCT No.: PCT/EP93/00376

§ 371 Date: Apr. 22, 1994

§ 102(e) Date: Apr. 22, 1994

[87] PCT Pub. No.: WO93/16379

PCT Pub. Date: Aug. 19, 1993

[30] Foreign Application Priority Data

Feb. 18, 1992 [DE] Germany .................. 42 04 850.8

[51] Int. Cl.$^6$ ................................................ G01N 27/407
[52] U.S. Cl. .................... 73/23.31; 73/31.05; 204/426
[58] Field of Search ........................ 73/23.31, 23.32, 73/31.05, 31.06; 338/34, 228, 229, 232, 233, 234, 252, 256, 317, 322; 204/424, 426, 428

[56] References Cited

U.S. PATENT DOCUMENTS 4,784,743  11/1988  Iino et al. .................... 204/425
5,098,548  3/1992  Duce ............................ 204/424
5,238,551  8/1993  Katsu et al. .................. 204/426
5,246,562  9/1993  Weyl et al. ................... 204/428

*Primary Examiner*—Michael J. Brock
*Attorney, Agent, or Firm*—Max Fogiel

[57] ABSTRACT

A housing (5) gas sensors, preferably lambda probes for detecting the content of pollution or oxygen or both in exhaust from, preferably, internal-combustion engines. A protective outer housing has electric connections at one end for a sensor mounted on a metal. A perforated protective cap accommodates the sensor and is intended for exposure to the gas being analyzed at the other end. A ceramic shape accommodates the connections and/or the metal and is accommodated in turn in the outer housing. The ceramic shape consists of at least two halves with a slot that is open along one side at the first end and with contacts resting flat against the base and walls of the slot with one side elevated above the open side. Each half also accommodates a depression extending all the way to the other end with the metal fitting into the depressions. At least the projecting areas of the contacts are in the vicinity of the depression. The connections are on the back of the contacts.

25 Claims, 2 Drawing Sheets

HOUSING FOR GAS SENSORS

BACKGROUND OF THE INVENTION

The present invention concerns a housing for gas sensors. Such a housing is known from German 3 410 122 A1.

One drawback to the known housing is its many separate components, which make it complicated and hence expensive to assemble. Although it does include a two-part ceramic shape, it is divided along a plane perpendicular to the axis of the overall housing. The housing must accordingly be assembled axially. The contacts are slipped over the plate-like member, producing a notching effect and the risk of damaging the metal, which the actual sensor is mounted on. The many structures required for securing the plate-like member and the separate electric connections also contribute to the complexity of assembly.

SUMMARY OF THE INVENTION

The object of the present invention is accordingly to make a generic housing for gas sensors as recited in the preamble to the major claim simpler and easier to assemble.

The object is surprisingly attained in accordance with the invention in a generic housing as recited in the preamble to the major claim by the characteristics recited in the body of that claim.

A housing with a ceramic shape consisting of preferably only two similar halves is simpler to manufacture. The plate-like member is inserted between the halves and the contacts into the open slots. The halves are, in contrast to the state of the art, joined radially and are inserted into the housing in that state. There are no such relative motions as forcing the contacts over the plate-like member in accordance with the present invention. The risk of damage during assembly is accordingly minimized. The result is a simple and easy-to-assemble housing and very little waste.

To eliminate errors due to outside air entering either such a pressurized environment as an exhaust pipe or such an evacuated environment as the flue in a heating system or analysis tube, the actual detection point, specifically the front of the plate-like member, is sealed off gas tight from the rear of the housing. It is preferred to establish the seal from outside by way of a contact between two conical sealing surfaces. The seal can be further tightened with additional sealing lips or annular seals or both to force the convex conical surface against the concave conical inner surface of the threaded bushing. The tightness between the cone and the plate-like member can be further increased by cement or glazing or by packing the convexity with (ceramic) powder, preferably in funnel-shaped depressions near where the plate-like member to be accommodated emerges.

It is of particularly great advantage to test and assemble the not yet completely finished gas sensor without disturbance from electric connections in the form of cables. It is also possible to provide connections in accordance with each customer's specific needs, simplifying maneuvering and adaptation to his specific application. The housing can then be finally assembled subsequent to preliminary assembly and testing in that the areas of the contacts extending beyond one side of the housing half, integrated along with the electric connections into a plug, are thrust over or into a separate protective housing with a socket on separated connecting cable. The product can then be finished by either the manufacturer or the customer once the probe has been inserted. The separated protective housing can then be manufactured with the protective housing already in place, by for example snapping, welding, or screwing it together, by securing it with specially designed clips, or otherwise.

Advantageous embodiments and advanced versions of the invention are recited in the subsidiary claims.

BRIEF DESCRIPTION OF THE DRAWINGS

One preferred embodiment of the invention will now be specified with reference to the drawing, wherein.

DESCRIPTION OF THE PREFERRED EMBODIMENTS

Figure 1:
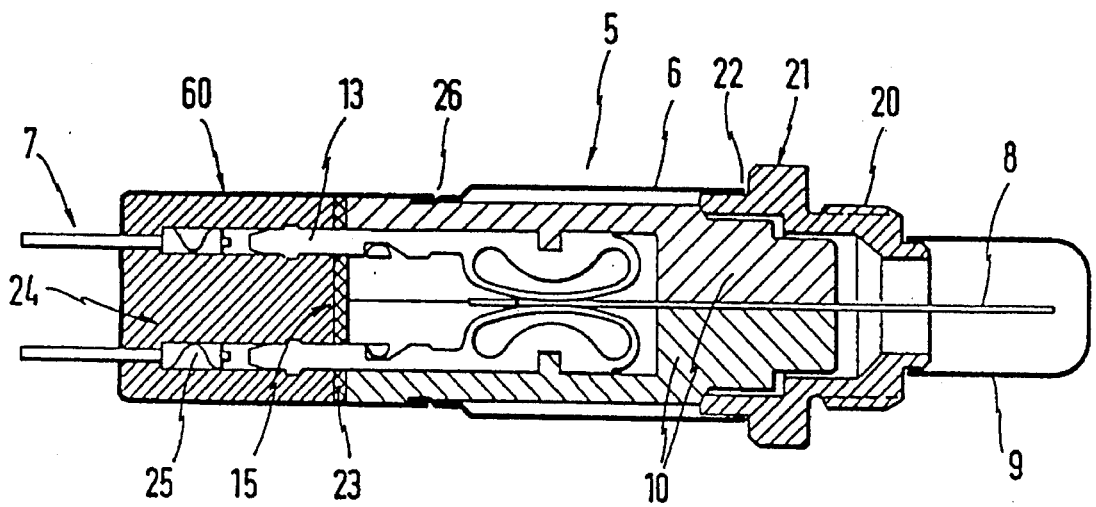
FIG. 1 is a schematic longitudinal section through one embodiment of the housing with the contacts in place and with a sensor resting on the plate-like member.

The gas-sensor housing 5 illustrated in FIG. 1 is accommodated in a protective outer housing 6. At one end of outer housing 6 are electric connections 7 leading to the sensor. The unillustrated sensor is mounted on a plate-like member 8. The other end of plate-like member 8, the end with the sensor, is accommodated within a perforated protective cap 9. Cap 9 is exposed to the gas being analyzed. Outer housing 6 also accommodates a ceramic shape 10 that in turn accommodates connections 7 and plate-like member 8.

Figure 2:
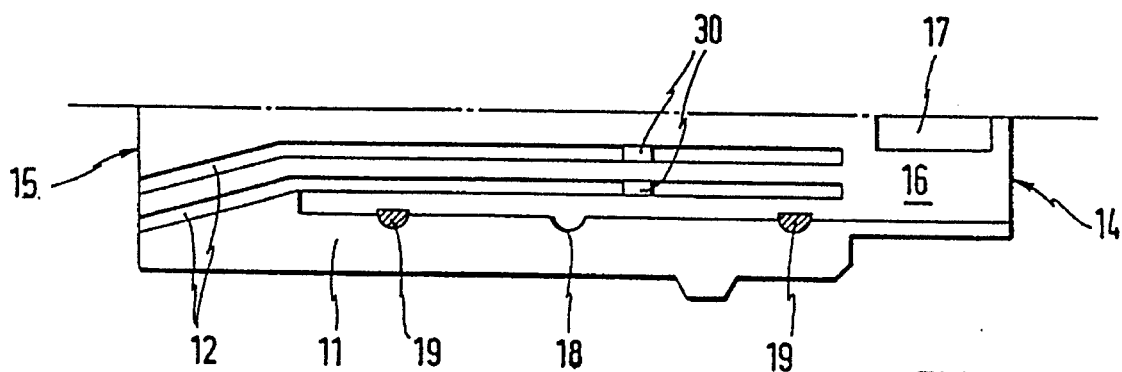
FIG. 2 is a schematic top view of the ceramic shape from FIG. 1.
Figure 3:
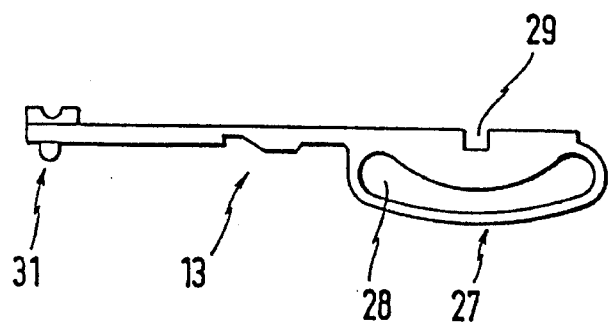
FIG. 3 illustrates one of the contacts illustrated in FIG. 1.
Figure 4:
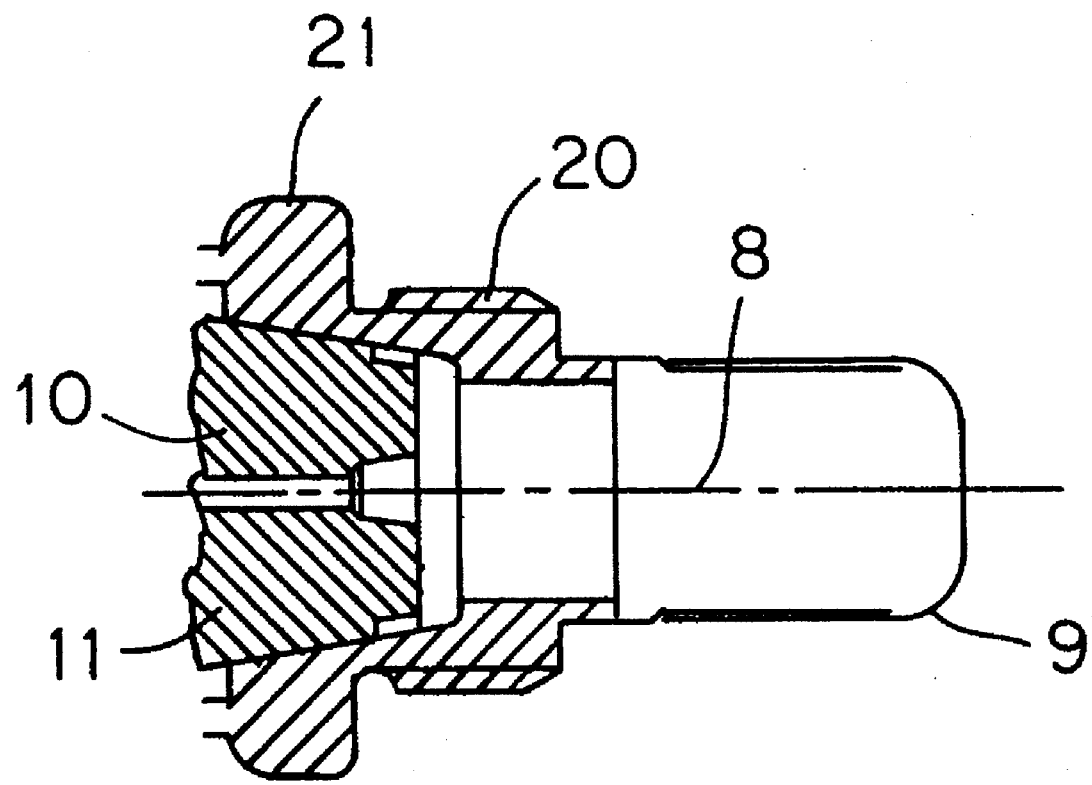
FIG. 4 is a partially broken away schematic cross sectional view showing another embodiment of the present invention.

The ceramic shape 10 in the present embodiment comprises two similar halves 11. One half 11 is viewed in FIG. 2 along the plane of separation, which is identical with the plane of projection. There are slots 12 in this surface at one end 15 of half 11. One side of the slots is open. An electric contact 13 like the contact illustrated in FIG. 3 is inserted in each slot 12. Contacts 13 rest flat against the base and walls of the slots with one side elevated above the open side.

Each half 11 also accommodates a depression 16 extending all the way to end 14, the end opposite end 15. Plate-like member 8 fits into depressions 16.

At least the areas of contacts 13 that project beyond the end 15 of half 11 are in the vicinity of depression 16. Plate-like member 8 is clamped between the depressions 16 in the two halves 11 that constitute ceramic shape 10. The sensor on plate-like member 8 is electrically connected. A simple electric connection is established by connecting, preferably crimping, connections 7 to contacts 13. It is of particular advantage for the contacts to be rest against each side of plate-like member 8, providing a number of adjacent contacts and hence electric connections 7. Each side of the metal will accordingly simultaneously be subject to uniform mechanical stress.

The two identical halves 11 of ceramic shape 10 are secured stationary by outer housing 6, which is in the form of a metal sleeve. Each half 11 has a contact surface (along the plane of projection of FIG. 2). The two contact surfaces secure both plate-like member 8 and contacts 13 between them in the assembled product. There is an adhesive accommodation 17 in the form of a sink in the vicinity of depression 16 and outside the vicinity of the slots. Each half 11 also has assembly guides 18 that fit into matching depressions on the other half. It is of advantage for the protective outer housing 6 to accommodate a holder for holding together the two halves 11 of ceramic shape 10. The holder can be a resilient ring, or a slotted or shrunk-on sleeve.

Housing 5 has screw-in bushing 21 with a thread 20. Cap 9 extends out of bushing 21. Outer housing 6 is secured to bushing 21, preferably welded to area 22.

A socket 24 is preferably attached to outer housing 6 by way of a stack 23 of springs. Connections 7 connect to contact 13 by way of a plug 25 that fits into socket 24. Outer housing 6 can also accommodate socket 24. It is, however, alternatively possible to provide another protective housing 60, folded, welded, or cemented to the actual outer housing 6 at an area 26.

The areas of contact 13 that extend beyond the end 15 of half 11 make it possible to test, assemble, and otherwise finish the sensor without interference from connections in the form of cables. The process will accordingly be simpler. Only at the very end will socket 24 and plug 25 be inserted and connected and separate protective housing 60 secured to outer housing 6.

Each contact 13 has a reversed projection 27 elevated above the open side of slots 12. Projection 27 is rendered resilient by a more or less arched stamped-out area 28. The resilience can alternatively be derived by slitting the area of contact 13. Contact 13 is also secured in slot 12 by a stamped-out notch 29 engaged by a projection 30 on each half 11 of ceramic shape 10.

This embodiment of the housing can be varied even further. The two ceramic halves for example need not be identical but just similar and can be secured together by an annular holder. A cone can also be secured to the other end of the ceramic shape and rest against a matching concave surface in the screw-in bushing to keep contaminating outside air away from the detection site under the protective cap. A funnel-shaped depression where plate-like member 8 emerges at each end of the cone is also practical. The depressions allow gas-tight connection by cementing or glazing, or by packing with (ceramic) powder and stuffing.

The cone can also be connected to the ceramic shape by a spacing sleeve.

The contact can also be produced not by stamping but by bending a piece of spring steel. The contact can rest on a shackle against projection 30 in the slot 12 in half 11. The end of an electric-connection sleeve rests against the other side of projection 31 and prevents contact 13 as a whole from sliding back and forth in slot 12.

We claim:

1. A housing for gas sensors having lambda probes for detecting the content of pollution or oxygen or both in exhaust from internal-combustion engines, comprising: a protective outer housing with electric connections at one end thereof for a sensor mounted on a plate-like member; a perforated protective cap at the other end of said protective outer housing and accommodating said sensor for exposure to a gas being analyzed; a ceramic shape holding means for securing to said electric connections; said ceramic shape comprising at least two halves, each of said halves having a slot at said one end of said outer housing; contacts resting flat against a base and walls of each said slot with one side elevated above an open side; each half of said ceramic shape also accommodating a depression extending from said one end to said other end of said protective outer housing; with said plate-like member fitting into the depressions of said two halves of said ceramic shape; at least projecting areas of said contacts being in said depression, said connections being connected to said contacts.

2. A housing as defined in claim 1, wherein said outer housing is a sleeve of heat-stable material.

3. A housing as defined in claim 2, wherein said heat-stable material is metal.

4. A housing as defined in claim 1, wherein said two halves of said ceramic shape are similar.

5. A housing as defined in claim 4, wherein each half of said ceramic shape has a contact surface; the two contact surfaces accommodating said plate-like member and said contacts in said housing between them.

6. A housing as defined in claim 1, wherein said two halves of said ceramic shape are identical.

7. A housing as defined in claim 1, wherein each half of said ceramic shape has assembly guides for said plate-like member and for securing the halves of said ceramic shape.

8. A housing as defined in claim 7, said assembly guides on one said half fit into matching depressions in the other half once the housing has been assembled.

9. A housing as defined in claim 1, wherein the two halves of said ceramic shape are secured together by an annular holder.

10. A housing as defined in claim 9, wherein said annular holder is a resilient ring.

11. A housing as defined in claim 9, wherein said annular holder is a slotted sleeve.

12. A housing as defined in claim 9, wherein said annular holder is a shrunk-on sleeve.

13. A housing as defined in claim 1, wherein each of said contacts has a reversed connections area with an adjacent contact area.

14. A housing as defined in claim 13, wherein said contact area comprises a projection projecting beyond the open side of said slot and being resilient in a part of the contact area.

15. A housing as defined in claim 13, wherein said contact area is resilient.

16. A housing as defined in claim 1, wherein said slot has at least one projection from said halves on said base for securing said contact with a stamped out notch.

17. A housing as defined in claim 1, wherein said slot has at least one projection from said halves on said base for securing said contact with a shackle.

18. A housing as defined in claim 1, wherein said outer housing is connected to a separate housing.

19. A housing as defined in claim 1, wherein the housing has a screw-in bushing for securing said gas sensor to said housing and for accommodating said protective cap, said bushing having a thread.

20. A housing as defined in claim 19, wherein said outer housing is secured to said bushing.

21. A housing as defined in claim 19, wherein one of said halves has at said other end a cone secured tight to a matching concave surface inside said bushing.

22. A housing as defined in claim 21, wherein said cone has depressions at each end where said plate-like member emerges.

23. A housing as defined in claim 22, wherein said depressions are funnel shaped.

24. A housing as defined in claim 21, wherein said two halves and respective cone are secured by an annular holder.

25. A housing for gas sensors having lambda probes for detecting the content of pollution or oxygen or both in exhaust from internal-combustion engines, comprising: a protective outer housing with electric connections at one end thereof for a sensor mounted on a plate-like member; a perforated protective cap at the other end of said protective outer housing and accommodating said sensor for exposure to a gas being analyzed; a ceramic shape holding means for securing to said electric connections; said ceramic shape comprising two halves, each of said halves having a slot at said one end of said outer housing; contacts resting flat against a base and walls of each said slot with one side elevated above an open side; each half of said ceramic shape also accommodating a depression extending from said one end to said other end of said protective outer housing; with said plate-like member fitting into the depressions of said two halves of said ceramic shape; at least projecting areas of said contacts being in said depression, said connections being connected to said contacts.

* * * * *